United States Patent [19]

Kissinger

[11] Patent Number: 4,902,836

[45] Date of Patent: Feb. 20, 1990

[54] PROCESS FOR INHIBITING DIHYDRIC PHENOL DEGRADATION AND COLOR FORMATION AND COMPOSITION THEREOF

[75] Inventor: Gaylord M. Kissinger, Evansville, Ind.

[73] Assignee: General Electric Company, Mt. Vernon, Ind.

[21] Appl. No.: 217,025

[22] Filed: Jul. 11, 1988

[51] Int. Cl.$^4$ .................. C07C 37/00; C07C 37/68; C07C 37/16

[52] U.S. Cl. .................................. 568/702; 568/724

[58] Field of Search ............................ 568/702, 724

[56] References Cited

U.S. PATENT DOCUMENTS 3,305,520 2/1987 Fritz et al.
3,402,186 9/1968 Schlichting et al. ............ 568/702
3,422,030 1/1969 Riley ............................. 568/702

FOREIGN PATENT DOCUMENTS 0144558 12/1978 Japan ............................ 568/702

OTHER PUBLICATIONS

Halasa et al., "Chemical Abstracts", vol. 90:55667m, (1979).

Primary Examiner—Werren B. Lone
Attorney, Agent, or Firm—Martin B. Barancik

[57] ABSTRACT

A process which comprises the addition of a dihydric phenol degradation inhibiting and color inhibiting effective amount of a phosphite to a composition comprising a dihydric phenol, phenol, and isomers of the dihydric phenol, said addition occurring prior to a distillation procedure.

12 Claims, No Drawings

PROCESS FOR INHIBITING DIHYDRIC PHENOL DEGRADATION AND COLOR FORMATION AND COMPOSITION THEREOF

BACKGROUND OF THE INVENTION

The dihydric phenols have achieved significant success in their commercial applications. Dihydric phenols are useful in the commercial manufacture of various polymers including the polyarylates, polyamides, epoxies, polyetherimides, polysulfones and the polycarbonates. Significant attention has been directed to the commercial preparations of the dihydric phenols. For many years it has been well known that the acid catalyzed reaction of phenol with specific aldehyde or ketone could prepare the 4,4'-dihydric phenol with specific groups derived from the aldehyde or the ketone connecting the two phenolic rings. In particular when phenol is reacted with acetone, the dihydric phenol 4,4'(dihydroxyphenyl)propane-2, hereafter known as bisphenol-A is formed. This has particular utility in polycarbonates, polyarylates and copolyestercarbonates as well as epoxies. In order to make certain polymers, in particular the polycarbonates, the bisphenol-A must be particularly pure, for example, as measured by color. Additionally, the process should be particularly efficient since the dihydric phenol costs contribute substantially to the cost of the final polymer. Therefore much attention has been directed to the recovery of bisphenol-A after preparation. Not only is recovery from the major stream containing large quantities of bisphenol-A important, but because of the economics involved, various side streams or "purge streams" also containing significant quantities of bisphenol-A should also be investigated for improved recovery techniques.

However, in the downstream processing of the composition prepared from the acid catalyzed condensation reaction, a loss in the quantity of desired dihydric phenol and a reduction in the color quality of the dihydric phenol composition has been observed when mixtures of the desired dihydric phenol, phenol and isomers of the desired dihydric phenol are separated in conventional distillation trains to recover the desired dihydric phenol. Generally, without an additive, portions of these materials readily degrade to a very dark color and undergo substantial chemical degradation. Significant reductions of the desired dihydric phenol, usually bisphenol-A, are observed.

It has now been found that this degradation of desired dihydric phenol as well as the color formation can be substantially inhibited by the addition of a phosphite or phosphonite to the composition comprising dihydric phenol, phenol and isomers of the dihydric phenol prior to the distillation step.

SUMMARY OF THE INVENTION

In accordance with the invention, there is a process which comprises the addition of a dihydric phenol degradation inhibiting and color inhibiting effective amount of a phosphite or phosphonite to a composition comprising a dihydric phenol, phenol, and isomers of the dihydric phenol, said addition occurring prior to a distillation procedure.

A further aspect of the invention is a composition comprising a dihydric phenol, phenol and isomers of the dihydric phenol in admixture with a dihydric phenol degradation inhibiting and color inhibiting effective amount of a phosphite or phosphonite.

DETAILED DESCRIPTION OF THE INVENTION

The most well known dihydric phenol is bisphenol-A. The invention is further described in detail with the production of bisphenol-A. However, any other dihydric phenol is expected to have the color and loss problems experienced with bisphenol-A if made from the acid catalyzed condensation reaction of a phenol with an acetone or aldehyde. Examples of such dihydric phenols include those in U.S. Pat. No. 2,999,835; 3,028,365; 3,334,154, and 4,131,575.

Phenol and acetone are passed into a reactor having an acidic catalyst system. In the past free hydrochloric acid was generally employed as the catalyst. However, because of equipment corrosion problems, solid ion exchange resin systems are also extensively employed. Such catalyst system is usually an Amberlite type resin obtained from Rohm and Haas. This resin has styrenic backbone with pendant $SO_3H$ groups which provide the acidic character to the resin. Usually the styrene is crosslinked with a small quantity of divinyl benzene or other crosslinking chemical. This addition of a crosslinker appears to provide structural strength and rigidity to the catalyst. Other ion exchange resins can also be used although it is preferable to use the styrenic backbone crosslinked with the difunctional monomer and having $SO_3H$ groups pendant from the aromatic nucleus of the styrene moiety. The phenol in excess, together with the acetone is passed over the acidic ion exchange resin. From thereon the bisphenol-A in the product stream can be recovered by a distillation train wherein the components bisphenol-A, phenol and isomers of dihydric phenol are separated due to their boiling point differences. Usually these distillations are done under vacuum because of the high boiling points of mixture components at atmospheric pressure.

Alternatively, after preparation the bisphenol-A can be initially separated by the formation of a phenol bisphenol-A adduct. This eliminates distillation separation of the major portion of bisphenol-A. However, minor portions of bisphenol-A in the purge stream are recovered by distillation.

In each of these processes, loss in yield of bisphenol-A and increased color is observed after distillation. The addition of a phosphite or phosphonite to the mixture of dihydric phenol, phenol and isomers of dihydric phenol bring about a significant reduction in the observed losses.

The term phosphite is used to include those phosphorous containing compounds which have the structure wherein phosphorous is attached to three oxygen atoms. Examples of such phosphite include those disclosed in Fritz U.S. Pat. No. 3,305,520; 3,673,146; 4,221,728; 4,335,039 and 3,809,676, all incorporated by reference in this specification. Phosphites of the formula below are generally preferred.

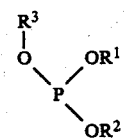

wherein $R_1$, $R_2$ and $R_3$ are the same or different and are alkyl or aryl. $R_3$ can also be hydrogen.

The phosphorous esters used in the practice of this invention are diesters or triesters obtained from phosphorous acid and alcohols or phenols. In the aforeindicated general formula, examples of $R_1$ and $R_2$ are respectively, an alkyl group such as butyl, hexyl, octyl, 2-ethylhexyl, nonyl, decyl, dodecyl, octadecyl, pentaerythrityl, cyclohexyl and the like, and an aryl group such as phenyl, tolyl, nonylphenyl and the like. $R^3$ represents hydrogen, or the above mentioned alkyl or aryl groups.

Examples of the phosphorous esters include tributyl phosphite, tris(2-ethylhexyl)phosphite, tridecyl phosphite, tristearyl phosphite, triphenyl phosphite, tricresyl phosphite, tris(nonylphenyl)phosphite, 2-ethylhexyldiphenyl phosphite, decyldiphenyl phosphite, phenyldi-2-ethylhexyl phosphite, phenyldidecyl phosphite, tricyclohexyl phosphite, distearylpentaerythrityl diphosphite, diphenylpentaerythrityl disphosphite, and the like.

Additionally, phosphonites are also included in this invention. A phosphonite is a tribonded phosphorous wherein phosphorous is attached to two oxygen atoms, the third phosphorous bond being through a hydrocarbon such as an alkyl or aryl group or a hydrogen. Examples of a phosphonite include those of the formula below.

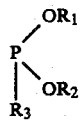

wherein $R_1$, $R_2$ and $R_3$ are defined as above.

Examples of a phosphite include phenyl diphenyl phosphonite and diphenol pentaerythritol phosphonite. Additional examples of phosphonites include those in U.S. Pat. No. 3,809,676; 3,978,020 and 4,221,728, all incorporated by reference.

Generally from about 0.01 to about 0.5 weight percent of the phosphite or phosphonite based upon the dihydric phenol, phenol, dihydric phenol composition is sufficient to bring about the reduction in dihydric phenol loss and color. Below this minimum, very little effect is observed. Above this maximum quantity, the additional positive effects generated are very minor and are usually offset by the increased cost. A preferred quantity of phosphite or phosphonite is from about 0.05 to about 0.3 weight percent.

Below are examples of the invention. These examples are not intended to limit the general inventive concept but merely illustrate the same. In the examples, the composition includes the following materials, P.P. in bisphenol-A, phenol is OH, O-P- is the orthopara isomer of bisphenol-A, "dimer" is IPP dimers, BPX-1 is a trisphenol, CR-1 is chroman-1, "spiro" is spirobiindane, IPP is isopropenylphenol, BPX-II is a further trisphenol.

The distillation proceeds at 240° C. At this temperature, phenol is distilled overhead while the bisphenol-A remains in the bottoms. The original composition and bottoms after distillation are analyzed by liquid chromatography. The color of the bottoms after distillation of the phenol is measured after distillation by placing a sample in methanol and measuring the ultraviolet absorption at 350 nm. The lower the number the lower the color. The first distillation, control, has no additive. The second distillation has 0.1 wt. % of the compound, tris(2,4-ditertiarylbutyl)phenyl phosphite. All the numbers are in grams. Below are the results.

EXAMPLE 1

|  | START | CONTROL, NO ADDITIVE | ADDITIVE |
|---|---|---|---|
| Start Temp | — | 240° C. | 240° C. |
| End Temp | — | 239.5° C. | 240° C. |
| Bottom | — | 174.3 | 172.9 |
| OH | 25.5 | 34 | 31.2 |
| P.P. | 128 | 126 | 127 |
| IPP | — | .048 | 0.36 |
| O.P. | 4.9 | 4.15 | 4.2 |
| Dimer | 1.1 | 1.3 | 1.4 |
| BPX-1 | 1.08 | 1.6 | 1.5 |
| CR-1 | 1.24 | 1.3 | 1.29 |
| SPIRO | .236 | .169 | .235 |
| BPX-II | 1.07 | 1.0 | 1.1 |
| % Loss BPA | — | 1.6 | 0.8 |
| Color Bottoms | — | 19. | 17.1 |

EXAMPLE 2

|  | START | CONTROL, NO ADDITIVE | ADDITIVE |
|---|---|---|---|
| Start Temp | — | 240° C. | 240° C. |
| End Temp | — | 239° C. | 240° C. |
| Bottom | — | 173.4 | 176.8 |
| OH | 257 | 31 | 34 |
| P.P. | 131.5 | 129 | 130.6 |
| IPP | .024 | .899 | 1.01 |
| O.P. | 4.7 | 4.2 | 4.1 |
| Dimer | 1.24 | 1.3 | 1.38 |
| BPX-1 | .624 | .884 | 1.01 |
| CR-1 | 1.4 | 2.89 | 1.32 |
| SPIRO | — | .674 | .668 |
| BPX-II | .356 | .253 | .541 |
| % Loss BPA | — | 1.9 | 0.7 |
| Color Bottoms | — | 19.1 | 17.7 |

EXAMPLE 3

|  | START | CONTROL NO ADDITIVE | ADDITIVE |
|---|---|---|---|
| Start Temp | — | 240° C. | 240° C. |
| End Temp | — | 238° C. | 240° C. |
| Bottom | — | 176.6 | 178 |
| OH | 253 | 35 | 35 |
| P.P. | 133 | 129.1 | 131.2 |
| IPP | — | .960 | .81 |
| O.P. | 4.5 | 3.71 | 4.0 |
| Dimer | .916 | 1.09 | .99 |
| BPX-1 | .972 | 1.8 | 1.0 |
| CR-1 | 2.3 | 1.6 | 1.6 |
| SPIRO | .096 | .088 | .07 |
| BPX-II | .764 | .561 | .783 |
| % Loss BPA | — | 2.94 | 1.3 |
| Color Bottoms | — | 26.4 | 20.0 |

As demonstrated in the above data, the loss of bisphenol-A is reduced by at least 50% in all the Examples. The color of the bisphenol-A fraction is significantly improved.

What is claimed is:

1. A process which comprises the addition of a bisphenol-A degradation inhibiting and color inhibiting effective amount of a phosphite or a phosphonite to a composition comprising biophenol-H, phenol, and isomers of bisphenol-A, said addition occurring prior to a distillaton procedure, said amount of phosphite being from 0.01 to 0.3 wt% of the composition.

2. The process in accordance with claim 1 wherein the material which inhibits the bisphenol-A degradation and color is a phosphite.

3. The process in accordance with claim 1 wherein the material which inhibits the bisphenol-A reduction and color is a phosphonite.

4. The process in accordance with claim 2 wherein the phosphite is of the structure

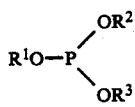

wherein $R^1$ and $R^2$ are the same or different and are alkyl, cycloalkyl or aryl and $R_3$ is hydrogen, alkyl, cycloalkyl or aryl.

5. The process in accordance with claim 3 wherein the phosphonite is of the structure.

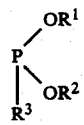

wherein $R^1$, $R^2$ and $R^3$ are defined as in claim 4.

6. The process in accordance with claim 4 wherein the phosphite is tris(2,4-ditertiarybutyl)phenyl phosphite.

7. A composition comprising bisphenol-A, phenol and isomers of bisphenol-A in admixture with a bisphenol-A degradation inhibiting and color inhibiting effective amount of a phosphite or phosphonite of from 0.01 to 0.3 wt% of the composition.

8. The composition in accordance with claim 7 wherein a phosphite is present.

9. The composition in accordance with claim 7 wherein a phosphonite is present.

10. The composition of claim 8 wherein the phosphite is of the structure

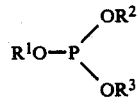

wherein $R^1$, $R^2$ and $R^3$ are defined as in claim 4.

11. The composition of claim 12 wherein the phosphonite is

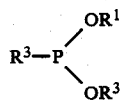

wherein $R^1$, $R^2$ and $R^3$ are defined as in claim 10.

12. The composition of claim 10 wherein the phosphite is tris(2,4-ditertiarybutyl)phenyl Phosphite.

* * * * *

UNITED STATES PATENT AND TRADEMARK OFFICE
CERTIFICATE OF CORRECTION

PATENT NO. : 4,902,836

DATED : February 20, 1990

INVENTOR(S) : Gaylord Michael Kissinger

It is certified that error appears in the above-identified patent and that said Letters Patent is hereby corrected as shown below:

```
Col. 5
Line 1
Cancel "biophenol-H" and add --bishpenol-A--

Col. 6
Line 22
Cancel "12" and add --9--
```

Signed and Sealed this

Fifth Day of February, 1991

Attest:

HARRY F. MANBECK, JR.

*Attesting Officer*     Commissioner of Patents and Trademarks